(12) United States Patent
Bonda et al.

(10) Patent No.: US 8,431,112 B2
(45) Date of Patent: *Apr. 30, 2013

(54) PHOTOSTABILIZATION OF CHOLECALCIFEROL WITH ALKOXYCRYLENE COMPOUNDS

(75) Inventors: Craig A. Bonda, Winfield, IL (US); Jean Zhang, Hickory Hills, IL (US)

(73) Assignee: Hallstar Innocations Corp., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/344,044

(22) Filed: Jan. 5, 2012

(65) Prior Publication Data

US 2012/0107255 A1    May 3, 2012

Related U.S. Application Data

(60) Continuation-in-part of application No. 13/294,339, filed on Nov. 11, 2011, now Pat. No. 8,257,687, which is a continuation-in-part of application No. 13/282,667, filed on Oct. 27, 2011, now Pat. No. 8,278,332, which is a division of application No. 12/533,598, filed on Jul. 31, 2009, now Pat. No. 8,070,989, which is a continuation-in-part of application No. 12/022,758, filed on Jan. 30, 2008, now Pat. No. 7,588,702, which is a continuation-in-part of application No. 11/891,281, filed on Aug. 9, 2007, now Pat. No. 7,597,825.

(51) Int. Cl.
*A61K 8/00* (2006.01)
*A61K 8/18* (2006.01)
*A61Q 17/04* (2006.01)
*F21V 9/04* (2006.01)
*F21V 9/06* (2006.01)
*G02B 5/22* (2006.01)
*G02B 5/26* (2006.01)
*A61K 38/43* (2006.01)

(52) U.S. Cl.
USPC .............. 424/59; 252/589; 424/60; 424/94.1; 424/401; 514/167; 514/690; 552/653

(58) Field of Classification Search .................. 252/589; 424/59, 60, 94.1, 401; 514/167, 690; 552/653
See application file for complete search history.

(56) References Cited

U.S. PATENT DOCUMENTS

| | | | |
|---|---|---|---|
| 2,623,060 A | 12/1952 | Cragoe | |
| 3,215,724 A | 11/1965 | Strobel et al. | |
| 3,337,357 A | 8/1967 | Strobel et al. | |
| 4,284,621 A | 8/1981 | Preuss et al. | |
| 4,293,542 A | 10/1981 | Lang et al. | |
| 4,307,240 A | 12/1981 | Ching | |
| 4,396,240 A | 8/1983 | Henson | |
| 4,562,278 A | 12/1985 | Hill | |
| 4,617,374 A | 10/1986 | Pruett et al. | |
| 4,707,537 A | 11/1987 | Pruett et al. | |
| 5,576,354 A | 11/1996 | Deflandre et al. | |
| 5,663,213 A | 9/1997 | Jones et al. | |
| 5,738,842 A | 4/1998 | Raspanti et al. | |
| 5,783,307 A | 7/1998 | Fagerburg et al. | |
| 5,989,528 A | 11/1999 | Tanner et al. | |
| 5,993,789 A | 11/1999 | Bonda et al. | |
| 6,113,931 A | 9/2000 | Bonda et al. | |
| 6,225,052 B1 | 5/2001 | Batz et al. | |
| 6,284,916 B1 | 9/2001 | Bonda et al. | |
| 6,485,713 B1 | 11/2002 | Bonda et al. | |
| 6,518,451 B2 | 2/2003 | Bonda et al. | |
| 6,537,529 B1 | 3/2003 | Bonda | |
| 6,551,605 B2 | 4/2003 | Bonda | |
| 6,800,274 B2 | 10/2004 | Bonda et al. | |
| 6,890,521 B2 | 5/2005 | Bonda | |
| 6,905,525 B2 | 6/2005 | Wood et al. | |

(Continued)

FOREIGN PATENT DOCUMENTS

DE    1222926    8/1966
EP    570838 A1    11/1993

(Continued)

OTHER PUBLICATIONS

"Amoco® NDC for Coatings, Inks and Adhesives" Amoco Chemicals, Bulletin FA-21b, dated Jun. 9, 2001.

(Continued)

*Primary Examiner* — Bijan Ahvazi
(74) *Attorney, Agent, or Firm* — Marshall, Gerstein & Borun LLP

(57) ABSTRACT

A method of reducing photodegradation of cholecalciferol when exposed to UV radiation in a composition containing cholecalciferol comprising combining with cholecalciferol a compound of formula (I) in an amount effective to quench excited state energy from cholecalciferol and transfer the excited state energy from cholecalciferol to the compound of formula (I),

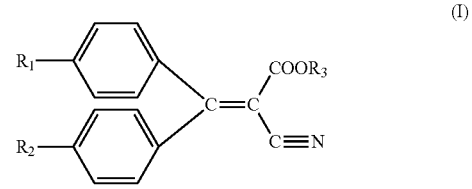

(I)

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical, thereby photostabilizing the cholecalciferol compound.

13 Claims, 4 Drawing Sheets

U.S. PATENT DOCUMENTS

| | | | |
|---|---|---|---|
| 6,919,473 | B2 | 7/2005 | Bonda et al. |
| 6,962,692 | B2 | 11/2005 | Bonda et al. |
| 7,064,114 | B2 | 6/2006 | Yiv et al. |
| 7,201,893 | B2 | 4/2007 | Wendel et al. |
| 7,235,587 | B2 | 6/2007 | Bonda et al. |
| 7,292,156 | B2 | 11/2007 | Smith et al. |
| 7,449,698 | B2 | 11/2008 | Nguyen et al. |
| 7,534,420 | B2 | 5/2009 | Bonda et al. |
| 7,588,702 | B2 | 9/2009 | Bonda et al. |
| 7,597,825 | B2 | 10/2009 | Bonda et al. |
| 2002/0127192 | A1 | 9/2002 | Murphy et al. |
| 2003/0000130 | A1 | 1/2003 | Wood et al. |
| 2003/0176542 | A1 | 9/2003 | Abe et al. |
| 2004/0047817 | A1 | 3/2004 | Bonda |
| 2004/0047818 | A1 | 3/2004 | Bonda |
| 2004/0057914 | A1 | 3/2004 | Bonda et al. |
| 2004/0170579 | A1 | 9/2004 | Mobius |
| 2004/0247539 | A1 | 12/2004 | Wendel et al. |
| 2005/0191249 | A1 | 9/2005 | Bonda et al. |
| 2006/0002869 | A1 | 1/2006 | Bonda et al. |
| 2006/0008426 | A1 | 1/2006 | Doring et al. |
| 2006/0062746 | A1 | 3/2006 | Brillouet et al. |
| 2006/0228311 | A1 | 10/2006 | Bonda et al. |
| 2007/0190005 | A1* | 8/2007 | Rozsa et al. ............ 424/70.1 |
| 2008/0286217 | A1 | 11/2008 | Chaudhuri |
| 2009/0057627 | A1 | 3/2009 | Bonda et al. |
| 2010/0135917 | A1 | 6/2010 | Winter et al. |

FOREIGN PATENT DOCUMENTS

| | | |
|---|---|---|
| EP | 0761201 A1 | 3/1997 |
| EP | 1323743 | 7/2003 |
| JP | 08225672 | 9/1996 |
| JP | 20050139263 | 6/2005 |
| SU | 1273360 | 11/1986 |
| WO | WO-00/27337 A2 | 5/2000 |
| WO | WO-02/42368 A2 | 5/2002 |
| WO | WO-2007/128840 A2 | 11/2007 |

OTHER PUBLICATIONS

"Light Absorbing Properties of Naphthalate Containing Polyesters" BP p.l.c., Technical Bulletin N-10, 1991.

Baussard, Jean-Francois, "Chap. II: Donor-Acceptor pairs for Forster Resonance Energy Transfer (FRET):" in Synthesis of New Ionic Functional Polymers by Free Radical Polymerization via the RAFT Process, Dissertation, Catholic University of Louvain, Jan. 26, 2004.

Bonda, "Research Pathways to Photostable Sunscreens," Cosmetics & Toiletries Magazine, 123:1, 49-60 (Feb. 5, 2008).

Chatelain et al., "Photostabilization of Butyl Methoxydibenzoylmethane (Avobenzone) and Ethylhexyl Methoxycinnamate by Bis-ethylhexyloxyphenol Methoxyphenyl Triazine (Tinosorb S), a New UV Broadband Filter", Photochemistry and Photobiology, 2003, vol. 74(3): pp. 401-406.

Cheung, P.-S. R., Roberts, C. W. "Photophysical Processes in Dimethyl 2,6-Naphthalenedicarboxylate and Poly(ethylene 2,6-Naphthalenedicarboxylate)" J. Polymer Sci.: Polymer Let. Ed., vol. 17, pp. 227-232 (1979).

European Search Report for EP 08 10 3204, dated Jul. 17, 2008.

European Search Report for EP 08 10 3205, dated Jul. 25, 2008.

Horiba Jobin Yvon Ltd., A Guide to Recording Fluorescence Quantum Yields, www.jyhoriba.co.uk, dated Jun. 3, 2003.

International Search Report for PCT/US/2008/058454, dated Sep. 23, 2008.

International Search Report for PCT/US2008/058456, dated Jun. 27, 2008.

Katritzky et al., "Synthesis of 3,3-diarylpyrrolidines from Diaryl Ketones", ARKIVOC, Gainesville, FL, United States, 2003, vol. 5, pp. 9-18, Arkat USA Inc. URL: http://arkatusa.org/zark/journal/2003/Bernath/GB-594J/594J.pdf.

Min et al., "Spectroscopic studies on the interaction of cinnamic acid and its hydroxyl derivatives with human serum albumin", J. Mol. Structure, 692:71-80 (2004).

Palm, M. D., O'Donoghue, M. N. "Update on Photoprotection" Dermatologic Therapy, vol. 20, pp. 360-376 (2007).

Senchenya et al., "Silicon-containing esters of α-cyanoacrylic acid: synthesis and properties", Russian Chem. Bul., 42:909-911 (1993).

Somsen et. al., "Planar chromatography coupled with spectroscopic techniques" in J. Chromatography A, vol. 703, 613-65 (1995).

Turro et al., Modern Molecular Photochemistry, University Science Books (1991).

Written Opinion of the International Searching Authority for PCT/US/2008/058454.

Written Opinion of the International Searching Authority for PCT/US2008/058456, dated Jun. 27, 2008.

Senchenya, N. G., et al. "Silicon-containing esters of α-cyanoacrylic acid: synthesis and properties" Russian Chem. Bul., vol. 42(5), pp. 909-911 (1993).

Bonda et al., "Photostabilization of Retinol and Retinyl Palmitate by Ethylhexyl Methoxycrylene," Cosmetics & Toiletries, vol. 126, No. 1, p. Cover, 40-48, Jan. 2011.

Bonda et al., "The Photostability and Photostabilization of trans-Resveratrol," Cosmetics & Toiletries, vol. 126, No. 9, p. 652-660, Sep. 2011.

* cited by examiner

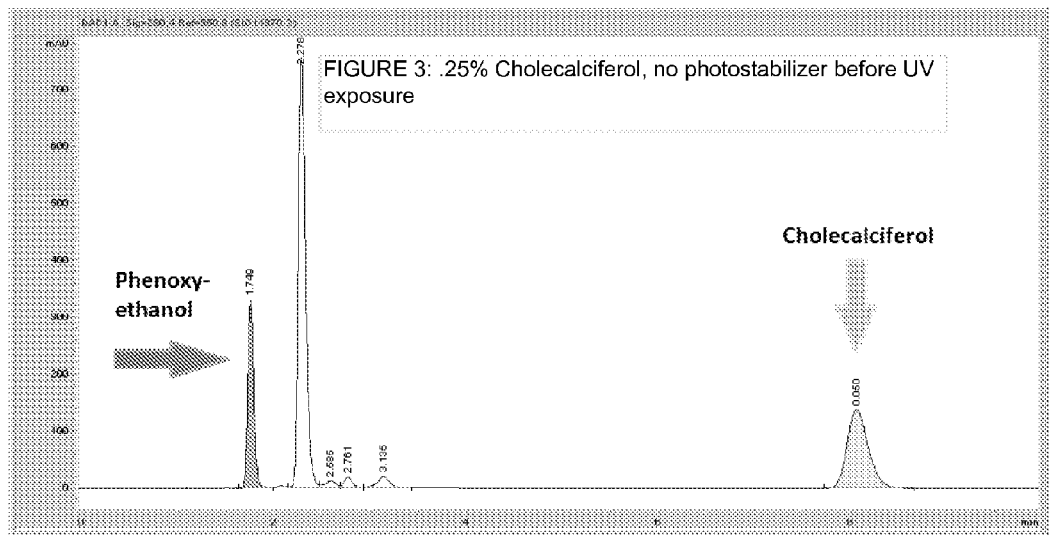
FIGURE 3: .25% Cholecalciferol, no photostabilizer before UV exposure
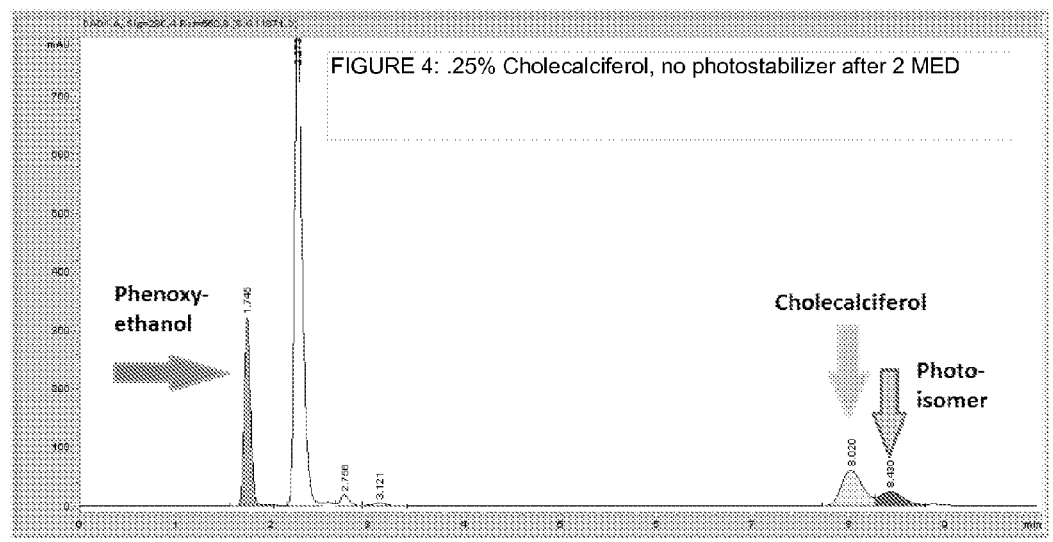
FIGURE 4: .25% Cholecalciferol, no photostabilizer after 2 MED

PHOTOSTABILIZATION OF CHOLECALCIFEROL WITH ALKOXYCRYLENE COMPOUNDS

CROSS-REFERENCE TO RELATED APPLICATION

This application is a continuation-in-part of U.S. Ser. No. 13/294,339, filed Nov. 11, 2011, which is a continuation-in-part of U.S. application Ser. No. 13/282,667, filed Oct. 27, 2011, which is a divisional of U.S. application Ser. No. 12/533,598, filed Jul. 31, 2009, which is a continuation-in-part of U.S. Pat. No. 7,588,702, issued Sep. 15, 2009, which is a continuation-in-part of U.S. Pat. No. 7,597,825, issued Oct. 6, 2009. The entire text of the priority application is incorporated herein by reference in its entirety.

FIELD OF THE INVENTION

The present invention is directed to compositions and methods to increase the photostability of cholecalciferol (CAS number 67-97-0). More particularly, the invention relates to the photostabilization of cholecalciferol with alkoxycrylene compounds.

BACKGROUND

Cholecalciferol (structure below), also called Calciol, is the mono-hydroxylated form of vitamin D, also called vitamin $D_3$.

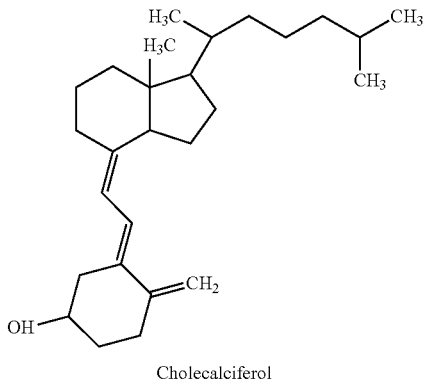 [SMILES: C=C1CCC(O)C/C1=C\C=C1\CCCC2(C)C1CCC2C(C)CCCC(C)C]

Cholecalciferol

Cholecalciferol is produced naturally by solar UVB (290-320 nm) irradiation of 7-Dehydrocholesterol in the skin. After synthesis in the skin, Cholecalciferol is hydroxylated in the liver to 25-Hydroxycholecalciferol (Calcifediol) which is hydroxylated again in the kidneys to 1,25-Dihydroxycholecalciferol (Calcitriol), the active hormonal form of Vitamin $D_3$. Cholecalciferol absorbs UV radiation with a peak at 265 nm and a molar extinction coefficient of 47,800. Its absorbance, though diminished in intensity after its peak, extends well into the solar UVB region (290-320 nm) as shown FIG. 2.

Cholecalciferol (Vitamin $D_3$) is a member of the Vitamin D group of fat-soluble secosteroids, molecules in which one of the bonds in the steroid structure has been broken. In humans, the body can synthesize Vitamin $D_3$ when sun exposure is adequate (hence its nickname, the "sunshine vitamin"). Unfortunately, skin protected from solar UV radiation by sunscreens is partly or completely prevented from producing Cholecalciferol. For that reason, it is often added to sunscreens and other skin care products in order to supplement its concentration in the epidermis where it is normally produced.

Following the final hydroxylation in the kidneys, calcitriol circulates as a hormone, regulating the concentration of calcium and phosphate in the bloodstream and promoting the healthy growth and remodeling of bone. Vitamin D prevents rickets in children and osteomalacia in adults, and, together with calcium, helps to protect older adults from osteoporosis. Vitamin D also affects neuromuscular function, inflammation, and influences the action of many genes that regulate the proliferation, differentiation and apoptosis of cells.

When exposed to sunlight, Cholecalciferol undergoes a destructive transformation of its double bonds to form a wide variety of photoisomers that have little if any biological activity on calcium metabolism. Therefore, the purpose of topically applying Cholecalciferol to skin—compensation for Cholecalciferol that is not produced in sunscreen-protected skin—is largely defeated, unless the Cholecalciferol itself is protected from photodegradation.

Vitamin $D_3$—cholecalciferol—is the form of Vitamin D that is obtained through human exposure to direct sunlight. It is considered to be superior to other forms of Vitamin D such as ergocalciferol, which is better known as Vitamin $D_2$. Research has shown that people in cold, rainy climates, are more susceptible to Vitamin D Deficiency, which has been scientifically linked to Seasonal Affective Disorder. This mean that people who live in places like Seattle, Wash., where the climate is often rainy and generally cold, are more likely to suffer from SAD, which is a type of seasonal depression that occurs primarily during the winter months.

A scientific link between low Vitamin $D_3$ levels and depression has been established following several recent studies confirming the relationship. According to one such study by scientists at Georgia State University: The likelihood of having depression in persons with vitamin D deficiency is significantly higher compared to those with vitamin D sufficiency. Early diagnosis and intervention are paramount because coexistence of vitamin D deficiency and depression has serious negative consequences on health.

Vitamin $D_3$ is produced in the skin when 7-dehydrocholestrol is irradiated by ultraviolet light (UBV) within the narrow wavelength limits of 290 to 315 nanometers. Once formed in the skin, it is carried to the liver where it is hydroxylated in a loosely regulated conversion to 25-hydroxy-cholecalciferol, then transported to the kidneys wherein, in a tightly regulated step, it is converted to 1,25-dihydroxycholecalciferol. Cholecalciferol has virtually no biological activity while 25-hydroxy-calciferol has roughly one one-thousandth the activity of 1,25-dihydroxycholecalciferol.

Although cholecalciferol clearly fits the definition of a hormone, which is defined as a substance produced in one body organ that exerts specific biological action in a target organ, it has long been classified as a vitamin because it is a small organic molecule that can be found in certain foods. It can best be described as a conditional nutrient, in the same category as coenzyme Q10, glutathione and glucosamine, which are small organic molecules that, under certain conditions, the body cannot synthesize in amounts sufficient to maintain health.

Compared to the current Daily Value recommendations of 200-400 IU per day for adults, 20 minutes of exposure to sunlight generates about 20,000 IU of cholecalciferol in a healthy adult. This is easily enough to avoid deficiency and build up the body's stores. Excessive exposure to sunlight does not lead to overproduction of vitamin D because continued sunlight exposure destroys vitamin $D_3$.

Thus, the direct application to the skin of a composition containing vitamin $D_3$, when the skin is exposed to sunlight, results in the vitamin $D_3$ being destroyed by photoreactions, at the same time that additional vitamin $D_3$ is being produced by the sunlight. Consequently, the packaging of the cholecalciferol product must be light fast. Even if cholecalciferol products are manufactured in the dark and stored in a light fast package, they quickly degrade upon application to the skin, rendering the cholecalciferol product much less effective.

SUMMARY

The photo-induced electronic excited state energy of cholecalciferol has been found to be readily transferred to (accepted by) α-cyanodiphenylacrylate compounds having an alkoxy radical in the four (para) position (hereinafter "alkoxycrylenes") on one of the phenyl rings having the formula (I):

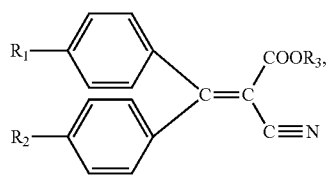

(I)

wherein one of $R_1$ and $R_2$ is a straight or branched chain $C_1$-$C_{30}$ alkoxy radical, preferably $C_1$-$C_8$, more preferably methoxy, and the non-alkoxy radical $R_1$ or $R_2$ is hydrogen; and $R_3$ is a straight or branched chain $C_1$-$C_{30}$ alkyl radical, preferably $C_2$-$C_{20}$.

It has surprisingly been found that the alkoxycrylene compounds of formula (I), described herein, significantly increase the photostability of cholecalciferol in a composition by 2 to 3-fold.

BRIEF DESCRIPTION OF THE DRAWINGS

FIG. 3 is a chromatogram of 0.25% cholecalciferol composition with no photostabilization, analyzed before exposure to UV radiation.

FIG. 4 is a chromatogram of the same formulation of FIG. 3, following irradiation with 15 W/m² (about 2 MED of direct sunlight)

DETAILED DESCRIPTION OF THE PREFERRED EMBODIMENTS

Figure 1:
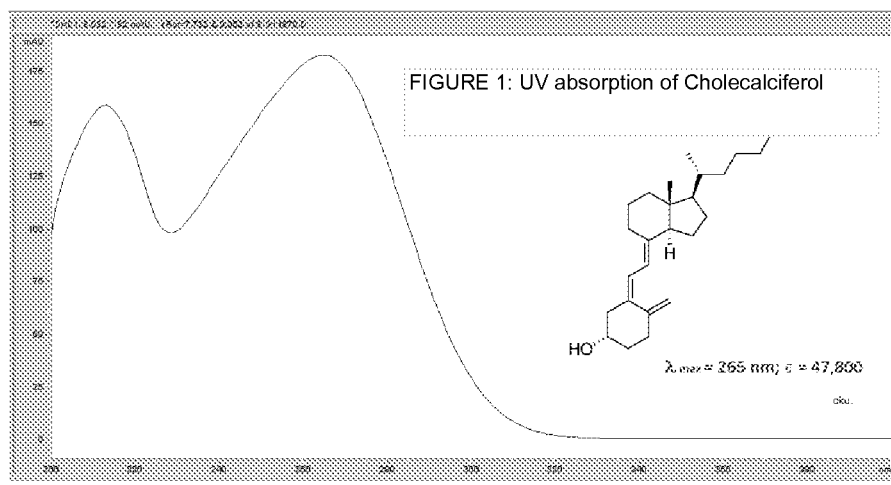
FIG. 1 is a graph showing the UV radiation absorption of cholecalciferol.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "alkoxy" herein refers to a radical extending from the para position of one or both of the phenyl rings having the formula O—R, wherein R is an alkyl radical, straight chain or branched having 1 to 30 carbon atoms, preferably wherein $R=C_1$ to $C_8$, more preferably $C_2$-$C_{20}$, and most preferably —O—$CH_3$ (methoxy). The oxygen atom of the alkoxy radical is covalently bonded to the para carbon atom of one or both of the phenyl rings, preferably only one of the phenyls, preferably having the formula (II) or (III):

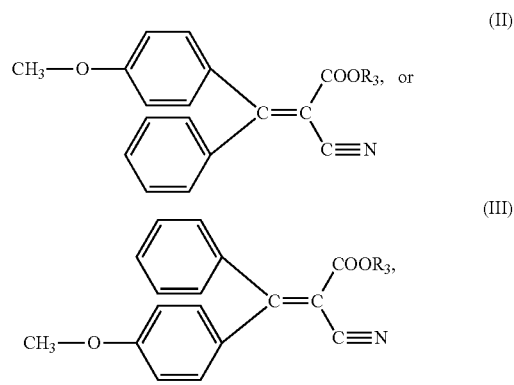

wherein $R_3$ is a straight or branched chain $C_1$-$C_{30}$ alkyl radical, preferably $C_2$-$C_{20}$.

The term "crylene" as used herein refers to a chromophoric moiety that includes an α-cyano-β,β-diphenyl propanoic acid ester.

The term "cyano" as used herein refers to a —C≡N group, also designated "—CN."

Topical compositions that contain cholecalciferol, as described herein, for treating one or more of the human conditions mentioned above, advantageously also may include UV-A and UV-B photoactive compounds in a dermatologically acceptable carrier, optionally including additives, such as emollients, stabilizers, emulsifiers, and combinations thereof. These additives can be used in preparing a UV filter composition, containing cholecalciferol in an emulsion (oil-in-water or water-in-oil) from a composition that includes one or more photoactive compounds and a solvent or a solvent combination that includes one or more organic solvents and water. When made, preferably the emulsion is an oil-in-water (O/W) emulsion, wherein the oil phase is primarily formed from a mixture of the UV filter compound(s) and one or more organic solvents.

The cholecalciferol-containing compositions advantageously, but optionally, include one or more photoactive compounds, in addition to the cholecalciferol compound, wherein the photoactive compound(s) act to absorb UV radiation, particularly UVB radiation. The alkoxycrylene compounds described herein accept electronic excited state energy from cholecalciferol compounds. The alkoxycrylenes also are very effective UVA absorbers in addition to providing electronic singlet state energy quenching of other UV-absorbing compounds in sunscreen compositions. As described in this assignee's pending application Ser. Nos. 11/891,281 and 12/022,758 filed on Aug. 9, 2007 and Jan. 30, 2008, respectively, the alkoxycrylene molecules described herein are especially effective photostabilizers when combined with one or more additional electronic singlet excited state quenching compounds such as oxybenzone. Particularly surprising photostabilization is achieved in cosmetic and dermatological compositions containing the alkoxycrylene compounds described herein together with octyl methoxycinnamate and Avobenzone, all of which are optionally useful, alone or in combination with the alkoxycrylene compounds of formula (I) and one or more coenzyme Q compounds, particularly cholecalciferol, as described herein.

In addition to photostabilizing cholecalciferol, the compounds of formula (I) are theorized to also photostabilize the following UV filters contained in cholecalciferol-containing compositions, including all of the following, including combinations of any two or more, and including compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxynaphthoic acid and its salts; n- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoylmethane, butylmethoxydibenzoylmethane, etocrylene, and 4-isopropyl-dibenzoylmethane).

The following UV filters, when optionally contained in cholecalciferol-containing compositions, should be particularly photostabilized by the alkoxycrylene molecules described herein: 2-ethylhexyl p-methoxycinnamate, 4,4'-t-butyl methoxydibenzoylmethane, octyldimethyl p-aminobenzoate, digalloyltrioleate, ethyl 4-[bis(hydroxypropyl)] aminobenzoate, 2-ethylhexylsalicylate, glycerol p-aminobenzoate, 3,3,5-trimethylcyclohexylsalicylate, and combinations thereof.

The photoactive cholecalciferol-containing compositions, disclosed herein for topical application to skin, can include a variety of additional photoactive compounds, preferably including one or more UV-A photoactive compounds and one or more UV-B photoactive compounds. Preferably, a cholecalciferol-containing composition also includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; uric acid derivatives; vilouric acid derivatives; tannic acid and derivatives thereof; hydroquinone; diethylamino hydroxybenzoyl hexyl benzoate and salts and derivatives thereof; and combinations of the foregoing.

UV A radiation (about 320 nm to about 400 nm), is recognized as contributing to causing damage to skin, particularly to very lightly colored or sensitive skin. A cholecalciferol-containing sunscreen composition preferably includes a UV-A photoactive compound. Preferably, a cholecalciferol-containing sunscreen composition includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

Commonly-assigned U.S. Pat. Nos. 6,485,713 and 6,537,529, the disclosures of which are hereby incorporated herein by reference, describe compositions and methods for increasing the photostability of photoactive compounds in a sunscreen composition, e.g., by the addition of polar solvents to the oil phase of a composition. In one embodiment of the cholecalciferol-containing compositions described herein, one or more of a highly polar solvent is present in the oil-phase of the composition. Preferably, a sufficient amount of a polar solvent is present in the cholecalciferol-containing topical compositions to raise the dielectric constant of the oil-phase of the composition to a dielectric constant of at least about 7, preferably at least about 8.

It has surprisingly been found that the alkoxycrylene compounds of formula (I) described herein unexpectedly and significantly increase the photostability of a cholecalciferol in a composition by about 2 to 3-fold. The ability of the alkoxycrylene compounds to stabilize cholecalciferol is theorized to be concentration dependent, with the amount of cholecalciferol photostabilization increasing with the concentration of the alkoxycrylene compound. For example, the percentages of cholecalciferol lost in compositions, with and without 5% ethylhexyl methoxycrylene, exposed to UV radiation comprising were 27.4% lost with 5% ethylhexyl methoxycrylene vs. 64.46% lost without the ethylhexyl methoxycrylene.

In accordance with one important topical composition embodiment, an alkoxycrylene compound of formula (I) is combined in a dermatological composition with a cholecalciferol. The total amount of cholecalciferol in the finished cholecalciferol-containing composition is chosen from about 0.01% by weight to about 5% by weight, preferably from about 0.1% by weight to about 2% by weight, more preferably from about 0.01% by weight to about 1.0% by weight, and most preferably about 0.1% to about 0.5%, in each case based on the total weight of the composition.

The alkoxycrylene compound is a compound of formula (I):

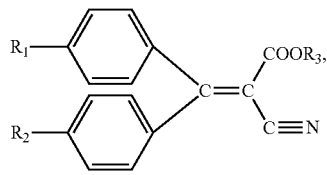

wherein one of $R_1$ and $R_2$ is a straight or branched chain $C_1$-$C_{12}$ alkoxy radical, and the non-alkoxy $R_1$ or $R_2$ is hydrogen and $R_3$ is a straight or branched chain $C_1$-$C_{24}$ alkyl radical. In a specific embodiment, the compound of formula (I) is ethylhexyl methoxycrylene (EHMC, IV).

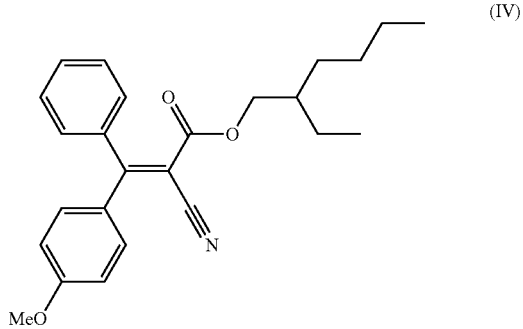 [SMILES: CCCCC(CC)COC(=O)/C(C#N)=C(\c1ccccc1)c1ccc(OC)cc1]

In another specific embodiment, the compound of formula (I) is butyloctyl methoxycrylene (BOMeOC, V).

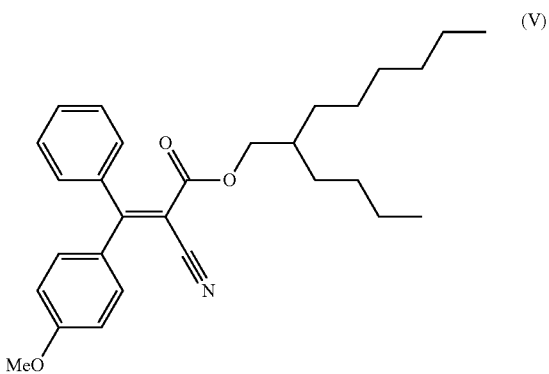 [SMILES: CCCCCCC(CCCC)COC(=O)/C(C#N)=C(\c1ccccc1)c1ccc(OC)cc1]

The total amount of the alkoxycrylene compound in the finished cholecalciferol-containing composition is chosen from the range of about 0.01% by weight to about 20% by weight, preferably from about 0.1 to about 10% by weight, for example from about 0.1% to about 5% by weight, in each case based on the total weight of the composition.

The molar ratio of the alkoxycrylene compound (formula (I)) to cholecalciferol in the finished cholecalciferol-containing composition is from about 1 to 1 to about 40 to 1. Typically, about 1 to 5 wt. % of Ethylhexyl methoxycrylene (compound of formula (I)) is used to photostabilize 0.1 to 0.5 wt. % cholecalciferol. Accordingly, the preferred range molar ratios of the alkoxycrylene compound to cholecalciferol compound is about 10 to 1 to about 55 to 1.

The cholecalciferol-containing compositions described herein can comprise cosmetic auxiliaries such as those conventionally used in such compositions, e.g. preservatives, bactericides, perfumes, antifoams, dyes, pigments which have a coloring effect, thickeners, moisturizers and/or humectants, fats, oils, waxes or other conventional constituents of a cosmetic or dermatological composition, such as alcohols, polyols, polymers, foam stabilizers, electrolytes, organic solvents or silicone derivatives.

Particularly advantageous cholecalciferol-containing compositions are also obtained when antioxidants are used as additives or active ingredients. According to this embodiment of the invention, the cholecalciferol-containing compositions advantageously comprise one or more antioxidants. Favorable, but nevertheless optional antioxidants which may be used are all antioxidants customary or suitable for cosmetic and/or dermatological applications.

The additional content of antioxidants may be included in the topically applied compositions described herein. According to this embodiment, favorable antioxidants which can be used together with cholecalciferol are any antioxidants suitable or conventional for topical cosmetic and/or dermatological applications.

The optional antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. alpha.-carotene, .beta.-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, .gamma.-linoleyl, cholesteryl and glyceryl esters thereof) and salts thereof, dilauryl thiodipropionate, distearyl thiodipropionate, coenzyme $Q_{10}$, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to .mu.mol/kg), and also (metal) chelating agents (e.g. .alpha.-hydroxy fatty acids, palmitic acid, phytic acid, lactoferrin), .alpha.-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. .gamma.-linolenic acid, linoleic acid, oleic acid), folic acid and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, .alpha.-glycosylrutin, ferulic acid, furfurylideneglucitol, carnosine, butylhydroxytoluene, butylhydroxyanisole, nordihydroguaiaretic acid, trihydroxybutyro-phenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention. Excellent results have been shown with an addition of both butyl hydroxy toluene at 0.01% to 0.5%, e.g., about 0.08%, and tocophenol at about 0.1% to about 0.5%, e.g., about 0.28%, based on the total weight of the composition.

The amount of antioxidants (one or more compounds) in the compositions is preferably about 0.001 to about 20% by weight, particularly preferably about 0.05 to about 10% by weight, in particular about 0.1 to about 10% by weight, based on the total weight of the composition.

If vitamin E and/or derivatives thereof are the antioxidant or antioxidants, it is advantageous to choose their respective concentrations from the range from about 0.001 to about 10% by weight, based on the total weight of the composition.

In accordance with another embodiment, the cholecalciferol-containing compositions containing an alkoxycrylene compound of formula (I) are combined with hydrophilic skin-care active ingredients and/or a broad-band UV filter compound and optionally, but preferably, together with a dibenzoylmethane derivative.

In another embodiment, advantageous hydrophilic active ingredients also may be added to the topically applied compositions. These hydrophilic compounds (individually or in any combinations with one another) are stabilized by their use together with an alkoxycrylene in a cholecalciferol-containing composition, according to this embodiment, include those listed below:

biotin; carnitine and derivatives; creatine and derivatives; folic acid; pyridoxine; niacinamide; polyphenols (in particular flavonoids, very particularly alpha-glucosylrutin); ascorbic acid and derivatives; Hamamelis; Aloe Vera; panthenol; coenzyme $Q_{10}$; amino acids.

Particularly advantageous hydrophilic active ingredients for the purposes of this embodiment are water-soluble antioxidants, such as, for example, vitamins.

The amount of hydrophilic active ingredients (one or more compounds) in the cholecalciferol-containing compositions is preferably about 0.0001 to about 10% by weight, particularly preferably about 0.001 to about 5% by weight, based on the total weight of the composition.

It is particularly advantageous when the cholecalciferol-containing compositions according to the present invention comprise anti-acne, anti-aging, wrinkle reducing, cosmetic or dermatological active ingredients, such as one or more cholecalciferol compounds.

Advantageous further active ingredients that are optionally included in topically-applied compositions include natural active ingredients and/or derivatives thereof, such as e.g. retinol, carotenoids, creatine, taurine and/or beta.-alanine.

Cholecalciferol-containing compositions may include known antiwrinkle active ingredients, such as flavone glycosides (in particular .alpha.-glycosylrutin), a retinoid, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

In accordance with still another important embodiment, an alkoxycrylene compound of formula (I) is combined in a cholecalciferol-containing anti-acne, anti-aging, wrinkle reducing, sunscreen or dermatological composition with particulate UV filter substances and/or a broad-band filter compound and optionally, but preferably, together with a dibenzoylmethane derivative and/or a dialkyl naphthalate UV filter compound.

Preferred particulate UV filter substances for the purposes of this embodiment of the present invention are inorganic pigments, especially metal oxides and/or other metal compounds which are slightly soluble or insoluble in water, especially oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

Zinc oxides for the purposes of this embodiment may also be used in the form of commercially available oily or aqueous predispersions Zinc oxide particles and predispersions of zinc oxide particles which are suitable according to the invention are distinguished by a primary particle size of <300 nm and can be obtained under the following proprietary names from the stated companies:

| Proprietary name | Coating | Manufacturer |
| --- | --- | --- |
| Z-Cote HP1 | 2% Dimethicone | BASF |
| Z-Cote | / | BASF |
| ZnO NDM | 5% Dimethicone | H&R |
| ZnO Neutral | / | H&R |
| MZ-300 | / | Tayca Corporation |
| MZ-500 | / | Tayca Corporation |
| MZ-700 | / | Tayca Corporation |
| MZ-303S | 3% Methicone | Tayca Corporation |
| MZ-505S | 5% Methicone | Tayca Corporation |
| MZ-707S | 7% Methicone | Tayca Corporation |
| MZ-303M | 3% Dimethicone | Tayca Corporation |
| MZ-505M | 5% Dimethicone | Tayca Corporation |
| MZ-707M | 7% Dimethicone | Tayca Corporation |
| Z-Sperse Ultra | ZnO (>=56%)/Ethylhexyl Hydroxystearate Benzoate/ Dimethicone/Cyclomethicone | Collaborative Laboratories |
| Samt-UFZO-450/D5 (60%) | ZnO (60%)/Cyclomethicone/ Dimethicone | Miyoshi Kasei |

Particularly preferred zinc oxides for the purposes of this embodiment are Z-Cote HP1 and Z-Cote from BASF and zinc oxide NDM from Haarmann & Reimer.

Titanium dioxide pigments useful in this embodiment may be in the form of both the rutile and anatase crystal modification and may for the purposes of this embodiment, advantageously be surface-treated ("coated"), the intention being for example to form or retain a hydrophilic, amphiphilic or hydrophobic character. This surface treatment may consist of providing the pigments by processes known per se with a thin hydrophilic and/or hydrophobic inorganic and/or organic layer. The various surface coatings may for the purposes of the present invention also contain water.

Inorganic surface coatings for the purposes of the particulate sunscreen additive embodiment may consist of aluminum oxide ($Al_2O_3$), aluminum hydroxide $AlOH_3$ or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may occur alone, in combination and/or in combination with organic coating materials.

Organic surface coatings for the purposes of the particulate sunscreen additive embodiment may consist of vegetable or animal aluminum stearate, vegetable or animal stearic acid, lauric acid, dimethylpolysiloxane (also: dimethicones), methylpolysiloxane (methicones), simethicones (a mixture of dimethylpolysiloxane with an average chain length of from 200 to 350 dimethylsiloxane units and silica gel) or alginic acid. These organic surface coatings may occur alone, in combination and/or in combination with inorganic coating materials.

Coated and uncoated titanium dioxides of the particulate sunscreen additive embodiment may be used in the form of commercially available oily or aqueous predispersions. It may be advantageous to add dispersion aids and/or solubilization mediators.

The cholecalciferol-containing cosmetic or dermatological compositions described herein may include conventional additives, solvents, and water concentrations when used for anti-acne, anti-aging, wrinkle reducing, cosmetic or dermatological treatment, care and cleansing of skin and/or the hair and as a make-up product in decorative cosmetics.

In accordance with another important embodiment, an alkoxycrylene compound of formula (I) is combined in a cholecalciferol-containing anti-acne, anti-aging, wrinkle reducing, sunscreen or dermatological composition with a lipophilic oxidation or UV-sensitive active ingredients and/or a broad-band filter compound and optionally, but preferably, together with a dibenzoylmethane derivative.

Advantageous lipophilic active ingredients which are stabilized in an excellent manner when used with the alkoxycrylenes described herein by the use according to the invention are those whose log P value is greater than 3.5. P is the partition coefficient, which is defined as the ratio of the equilibrium concentration of a dissolved substance in a two-phase system which consists of two solvents which are essentially immiscible with one another. These two solvents are, in the present case, n-octanol and water, i.e.

$$P_{ow} = \frac{C_{n-octanol}}{C_{water}}$$

It is advantageous to choose the lipophilic active ingredients from the group of plastoquinones. For the purposes of the present invention, cholecalciferol, is an excellent lipophilic compound, having a log P value of about 10.24.

Further lipophilic acid ingredients advantageous according to this embodiment of the invention are carotenoids. For the purposes of the present invention, beta.-carotene, which has a log P value of 15, for example, is particularly advantageous.

Further lipophilic active ingredients advantageous according to this embodiment of the invention are: lipoic acid and derivatives, vitamin E and derivatives, vitamin F, dioic acid [8-hexadecene-1,16-dicarboxylic acid (CAS number 20701-68-2)], and coenzyme $Q_{10}$.

The amount of lipophilic active ingredients (one or more compounds) in the compositions, in addition to cholecalciferol, is preferably about 0.0001 to about 10% by weight, particularly preferably about 0.001 to about 5% by weight, based on the total weight of the composition.

EXAMPLES

To test the effects of simulated solar UV radiation on Cholecalciferol, two test formulations were prepared, each containing 0.25% cholecalciferol. One formulation contained no photo stabilizer, the other contained 4% Ethylhexyl methoxycrylene (formula (I)). The compositions of the two formulations and the preparative procedure can be found in Table 1.

TABLE 1

Cholecalciferol Photostability Study

HPLC results

| | | Main compounds | | |
|---|---|---|---|---|
| | | 0.25% Cholecalciferol, no photostablizer | | 0.25% Cholecalciferol 4.0% SolaStay S1 |
| | | Cholecalciferol | Isomer | Cholecalciferol | Isomer |
| % Remaining, 15 W/m², one hour | | 44.42 | 55.58 | 100.0 | 0 |

Formulations

| | Ingredients | 0.25% Cholecalciferol | |
|---|---|---|---|
| | | no photostabilizer | with 4.0% SolaStay S1 |
| | Oil Phase | | |
| 1 | Isopropyl Myristate | 4.00 | |
| 1b | Ethylhexyl methoxycrylene | | 4.00 |
| 2 | Caprylic/capric triglycerides | 5.00 | 5.00 |
| 3 | Phenethyl benzoate | 5.00 | 5.00 |
| 6 | Butylated hydroxy toluene | 0.05 | 0.05 |
| 7 | Cholecalciferol | 0.25 | 0.25 |
| | Emulsifiers | | |
| 4 | Trideceth-12 | 1.00 | 1.00 |
| 5 | Behenyl alcohol, Glyceryl stearate, Glyceryl stearate citrate, Sodium dicocoylethylenediamine PEG-15 sulfate | 1.00 | 1.00 |
| 11 | Sodium lauroyl lactylate, Sodium dicocoylethylenediamine PEG-15 sulfate | 1.00 | 1.00 |
| | Water Phase | | |
| 8 | Water | 75.00 | 75.00 |
| 9 | Disodium EDTA | 0.05 | 0.05 |
| 10 | Xanthan gum | 0.15 | 0.15 |
| 12 | Glycerin | 4.00 | 4.00 |
| 13 | Phenoxyethanol, Caprylyl glycol, Chorphenesin | 1.00 | 1.00 |
| 14 | Acrylamide/Sodium acryloyldimethyl taurate copolymer | 2.50 | 2.50 |
| | Total | 100.00 | 100.00 |

Preparative procedure:
1. Charge large vessel with water (8). Dissolve 9. Add 10 and stir until fully incorporated.
2. Charge secondary vessel with 1-4. Heat to 65 degrees C. Add 5 and stir until homogeneous, and then add 6-7 and mix well.
3. To main vessel, add about ⅓ of water prepared in step 1. Add 11 with stirring and heat to 65 degrees C.
4. Add oil phase prepared in step 2. Homogenize until emulsion is fully formed. Slowly add balance of water prepared in step 1.
5. Stop homogenizing and then resume mixing and start cooling.
6. Premix 12 and 13 and add to batch. Add 13 and continue mixing until smooth and homogeneous.
7. Q.S. water to replace water lost during processing. Package when batch cools below 35 degrees C.

A sample of each test formulation was analyzed by HPLC for Cholecalciferol content before and after exposure to simulated solar radiation. Radiation was supplied by a Q-Sun Xe-1 xenon test chamber equipped with a Daylight B/B filter and a chiller unit to maintain temperature in the chamber below 30° C. Chromatographic analyses were performed on a Hewlett Packard Series 1100 HPLC System equipped with quaternary pumps, a vacuum degasser, an auto-injector, and a dynamic absorbance detector (DAD), connected to a computer running Chemstation for LC 3D (Agilent Technologies). Following are the conditions used for the chromatographic analyses of CoQ10 content in a topical lotion for contact against the skin:

Reagents:
1. Acetonitrile, HPLC grade
2. Tetrahydrofuran (THF), HPLC grade
3. Methanol, HPLC grade
4. Water, HPLC grade Preparation of Mobile Phase a and Mobile Phase B:

Mobile Phase A—10% THF in Acetonitrile was prepared by pipetting 50 ml THF into about 400 ml Acetonitrile in a 500 ml volumetric flask, mixing and bringing to volume with Acetonitrile.

Mobile Phase B—1% Methanol in water was prepared by pipetting 10 ml Methanol into about 950 ml water in a 1 L volumetric flask, mixing and bringing to volume with water.

B. Conditions

| Column: | Luna 5μ, C8 (2) 100A, 150 * 4.6 mm |
|---|---|
| Mobile Phase (A): | 10% THF in Acetonitrile |
| Mobile Phase (B): | 1% Methanol in water |
| Flow Rate: | 1.0 ml/min |
| Temperature: | 450 C. |
| Detector: | UV Spectrophotometer @280 nm |
| Injection | 8 μl |

Results:

Several new peaks appeared on the HPLC chromatograms taken after the samples were exposed to simulated sunlight. These new peaks are attributed to photoproducts resulting from the photodegradation of the Cholecalciferol. The locations of these new peaks are depicted in FIG. 4, which display the chromatograms taken after irradiation of the formulations containing no photostabilizer (FIG. 4) and 4% Ethylhexyl methoxycrylene (FIG. 5) respectively. One can see that photoproducts are much less prevalent in the chromatogram taken of the photostabilized formulation.

CONCLUSIONS

Cholecalciferol is highly sensitive to UV radiation. When incorporated into a skin care lotion that is applied to a substrate and exposed to a low dose of simulated solar radiation, cholecalciferol experiences rapid conversion to a photoisomer. Incorporation of the photostabilizer Ethylhexyl methoxycrylene in a formulation containing cholecalciferol completely prevents its photodegradation, thereby maintaining the topically applied cholecalciferol's bioavailability.

To test the effects of simulated solar UV radiation on Cholecalciferol, two test formulations were prepared for application of human skin, each containing 25% Cholecalciferol. One formulation contained no photostabilizer, the other contained 4% Ethylhexyl methoxycrylene. The compositions of the two formulations and the preparative procedure can be found in Table 2.

TABLE 2

Topically Applied Skin Care Lotion

| | Ingredients | 0.25% Cholecalciferol Batch Number | |
|---|---|---|---|
| | | JZ3-204 no photostabilizer | JZ3-205 with 4.0% SolaStay S1 |
| | Oil Phase | | |
| 1 | Isopropyl Myristate | 4.00 | |
| 1b | Ethylhexyl methoxycrylene | | 4.00 |
| 2 | Caprylic/capric triglycerides | 5.00 | 5.00 |
| 3 | Phenethyl benzoate | 5.00 | 5.00 |
| 6 | Butylated hydroxy toluene | 0.05 | 0.05 |
| 7 | Cholecalciferol | 0.25 | 0.25 |
| | Emulsifiers | | |
| 4 | Trideceth-12 | 1.00 | 1.00 |
| 5 | Behenyl alcohol, Glyceryl stearate, Glyceryl stearate citrate, Sodium dicocoylethylenediamine PEG-15 sulfate | 1.00 | 1.00 |
| 11 | Sodium lauroyl lactylate, Sodium dicocoylethylenediamine PEG-15 sulfate | 1.00 | 1.00 |
| | Water Phase | | |
| 8 | Water | 75.00 | 75.00 |
| 9 | Disodium EDTA | 0.05 | 0.05 |
| 10 | Xanthan gum | 0.15 | 0.15 |
| 12 | Glycerin | 4.00 | 4.00 |
| 13 | Phenoxyethanol, Caprylyl glycol, Chorphenesin | 1.00 | 1.00 |
| 14 | Acrylamide/Sodium acryloyldimethyl taurate copolymer | 2.50 | 2.50 |
| | Total | 100.00 | 100.00 |

Preparative procedure
1. Charge large vessel with water (8). Dissolve 9. Add 10 and stir until fully incorporated.
2. Charge secondary vessel with 1-4. Heat to 65 degrees C. Add 5 and stir until homogeneous, and then add 6-7 and mix well.
3. To main vessel, add about ⅓ of water prepared in step 1. Add 11 with stirring and heat to 65 degrees C.
4. Add oil phase prepared in step 2. Homogenize until emulsion is fully formed. Slowly add balance of water prepared in step 1.
5. Stop homogenizing and then resume mixing and start cooling.
6. Premix 12 and 13 and add to batch. Add 13 and continue mixing until smooth and homogeneous.
7. Q.S. water to replace water lost during processing. Package when batch cools below 35 degrees C.

A sample of each test formulation was analyzed by HPLC for Cholecalciferol content before and after exposure to simulated solar radiation. Radiation was supplied by a Q-Sun Xe-1 xenon test chamber equipped with a Daylight B/B filter and a chiller unit to maintain temperature in the chamber below 30° C. Chromatographic analyses were performed on a Hewlett Packard Series 1100 HPLC System equipped with quaternary pumps, a vacuum degasser, an auto-injector, and a dynamic absorbance detector (DAD), connected to a computer running Chemstation for LC 3D (Agilent Technologies). Following are the conditions used for the chromatographic analyses of Cholecalciferol content in a topical lotion for the skin:

A. Reagents
1. Acetonitrile, HPLC grade
2. Tetrahydrofuran (THF), HPLC grade
3. Methanol, HPLC grade
4. Water, HPLC grade Preparation of Mobile Phase a and Mobile Phase B:

Mobile Phase A—10% THF in Acetonitrile was prepared by pipetting 50 ml THF into about 400 ml Acetonitrile in a 500 ml volumetric flask, mixing and bringing to volume with Acetonitrile.

Mobile Phase B—1% Methanol in water was prepared by pipetting 10 ml Methanol into about 950 ml water in a 1 L volumetric flask, mixing and bringing to volume with water.

Conditions

| Column: | Luna 5μ, C8 (2) 100A, 150 * 4.6 mm |
|---|---|
| Mobile Phase (A): | 10% THF in Acetonitrile |
| Mobile Phase (B): | 1% Methanol in water |
| Flow Rate: | 1.0 ml/min |
| Temperature: | 450 C. |
| Detector: | UV Spectrophotometer @280 nm |
| Injection | 8 μl |

Pump Program:

| Time (min) | Mobile Phase A | Mobile Phase B |
|---|---|---|
| 0.0 | 92.0 | 8.0 |
| 2.0 | 92.0 | 8.0 |
| 4.5 | 99.8 | 0.2 |
| 18.0 | 99.8 | 0.2 |
| 22.0 (stop) | 92.0 | 8.0 |

Sample Preparation and Procedure (Performed Under Low Light Conditions)

Pre-Irradiated and Control Samples

Weigh about 0.2 grams of the test material to a 5 cm×5 cm roughened quartz plate (roughness=6 μm). Spread the test material evenly and keep the plate in dark for one hour.

Irradiated Samples

Apply approximately 0.2 grams of the test material to a 5 cm×5 cm roughened quartz plate. Spread the test material evenly. Irradiate the plate in the xenon test chamber with 15 W/m$^2$ TUV for one hour.

Sample Extraction

Add about 2 ml THF to rinse the sample from the plate twice. Mix well and filter through PTFE sample filters. Analyze by HPLC according to the method described above.

Calculation of Cholecalciferol Content

Calculate Cholecalciferol content using Tocopherol, included in the test formulations as an internal standard, by comparing the ratio of the areas of the Phenoxyethanol and Cholecalciferol peaks before and after irradiation.

Results:

| | Formulation# | | | |
|---|---|---|---|---|
| | JZ3-204 | | JZ3-205 | |
| | Main compounds | | | |
| | 0.25% Cholecalciferol, no photostablizer | | 0.25% Cholecalciferol 4.0% Ethylhexyl methoxycrylene | |
| | Cholecalciferol | Isomer | Cholecalciferol | Isomer |
| % Remaining after 15 W/m$^2$ UV for one hour | 44.42% | 55.58% | 100% | 0% |

For the formulation containing 25% and no photostabilizer, Phenoxyethanol, a component of the preservation system which served as the internal standard, eluted at 1.74 minutes, and Cholecalciferol eluted at 8 minutes. The ratio of the area of the Phenoxyethanol peak to the area of the Cholecalciferol peak was 0.6807 before irradiation and 1.5324 after irradiation. This calculates to a loss of Cholecalciferol of 55.58%, all of which is accounted for by the new peak which eluted at 8.43 minutes, as shown in FIG. 2.

For the formulation containing 25% Cholecalciferol and 4% Ethylhexyl methoxycrylene, Phenoxyethanol also eluted at 1.7 minutes and Cholecalciferol eluted at 7.9 minutes, both before and after irradiation. The ratio of the area of the Phenoxyethanol peak to the area of the Cholecalciferol peak was 0.65 before irradiation and 0.62 after irradiation. This calculates to a gain of Cholecalciferol of about 5%. Therefore, our assumption is that 100% of the Cholecalciferol was preserved from photodegradation by the presence of the photo stabilizer, Ethylhexyl methoxycrylene.

Figure 2:
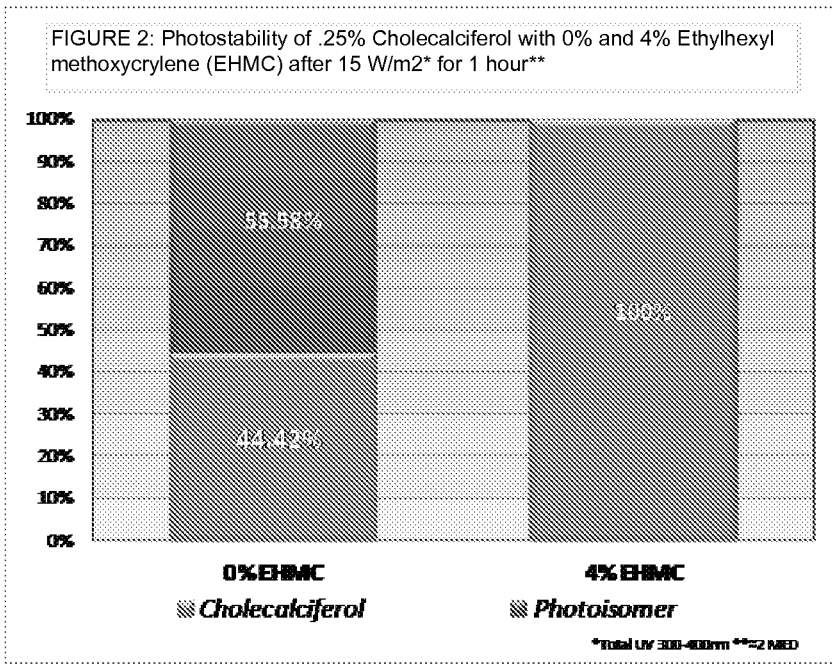
FIG. 2 is a bar graph showing the loss of 55.58% of cholecalciferol, when exposed to 15 W/m² UV radiation for one hour (equivalent to about 2 MED or minimal erythemal dose of direct sunlight) versus no loss with the addition of 4% compound of formula (I)

The results are displayed graphically in FIG. 2.

Figure 5:
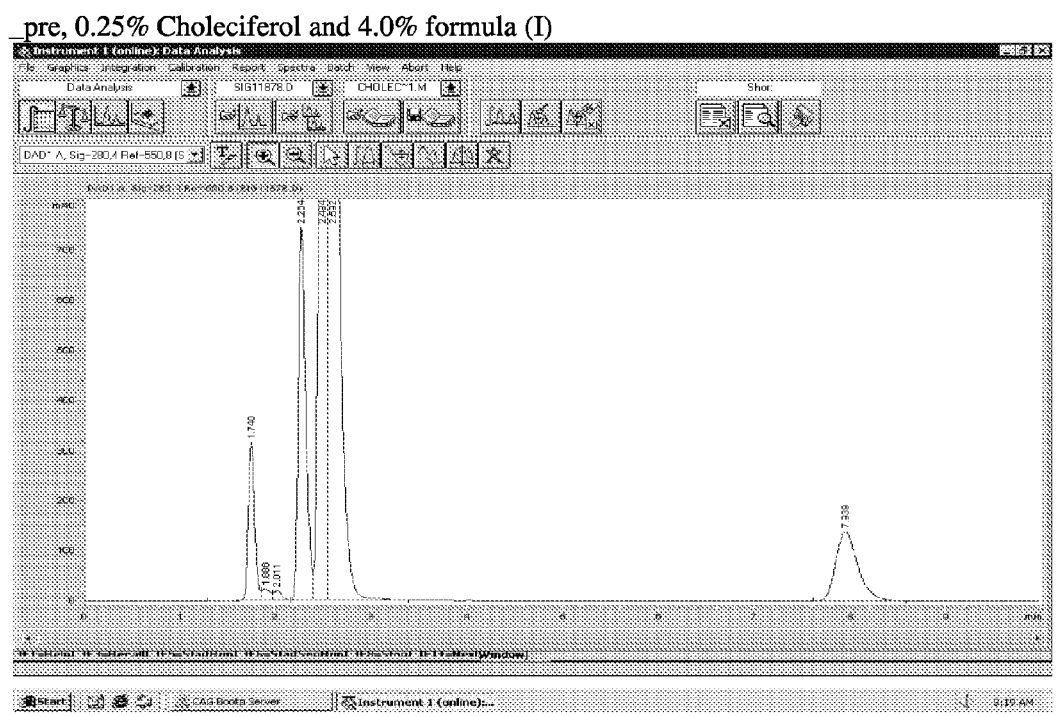
FIG. 5 is a chromatogram of the formulation of FIGS. 3 and 4 taken after irradiation of the formulation containing 4% ethylhexyl methoxycrylene and shows no photodegradation of the cholecalciferol.

FIG. 3 is the chromatogram of the 0.25% cholecalciferol formulation with no photostabilizer, analyzed before exposure to UV radiation. FIG. 4 is the chromatogram of the same formulation following irradiation with 15 W/m$^2$ (about 2 MED). The cholecalciferol peak is significantly diminished in area and a new peak elutes at 8.4 minutes. The new peak is attributed to a biologically inactive photoisomer. Its location is indicated in FIG. 4. FIG. 5 is the chromatogram taken after irradiation of the formulation containing 4% ethylhexyl methoxycrylene and shows no photodegradation of the cholecalciferol.

The invention claimed is:

1. A method of reducing photodegradation of cholecalciferol when exposed to UV radiation in a sunscreen or dermatological composition containing said cholecalciferol compound comprising combining with said cholecalciferol compound in an amount of about 0.01% to about 5% by weight and of formula (I) in an amount of about 0.1% to about 20% by weight, based on the total weight of the composition, to quench excited state energy from the cholecalciferol and transfer the excited state energy from the cholecalciferol compound to the compound of formula (I),

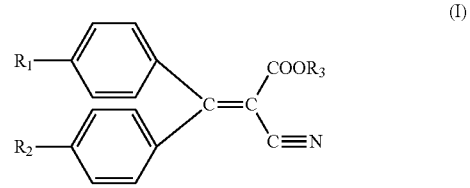

(I)

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical.

2. The method of claim 1, wherein $R_1$ is methoxy and $R_2$ is hydrogen.

3. The method of claim 1, wherein $R_1$ is hydrogen and $R_2$ is methoxy.

4. The method of claim 1, wherein $R_3$ is a $C_{12}$-$C_{24}$ straight chain or branched alkyl.

5. The method of claim 4, wherein $R_3$ is a 2-butyloctyl radical.

6. The method of claim 4, wherein $R_3$ is an 2-ethylhexyl radical.

7. The method of claim 1, wherein the compound of formula (I) is present in an amount in the weight range of about 0.1% to about 10%, based on the total weight of the composition.

8. The method of claim 1, wherein the compound of formula (I) is present in an amount in the weight range of about 0.1% to about 5%, based on the total weight of the composition.

9. The method of claim 1, wherein cholecalciferol is present in the weight range of about 0.01% to about 2%, based on the total weight of the composition.

10. The method of claim 1, wherein cholecalciferol is present in the weight range of about 0.01% to about 1.0%, based on the total weight of the composition.

11. The method of claim 1, wherein a molar ratio of the compound of formula (I) to cholecalciferol is about 1 to 1 to about 40 to 1.

12. The method of claim 11, wherein the molar ratio of cholecalciferol to the compound of formula (I) is about 0.01 to about 0.06.

13. The method of claim 1, wherein a molar ratio of compound of formula (I) to cholecalciferol is about 10 to 1 to about 55 to 1.

* * * * *